(12) United States Patent
Burd et al.

(10) Patent No.: US 8,747,473 B2
(45) Date of Patent: Jun. 10, 2014

(54) MODULAR LATERAL EXPANSION DEVICE

(75) Inventors: Timothy A. Burd, Omaha, NE (US); Mahmoud P. Abdelgany, Rockaway, NJ (US)

(73) Assignee: Custom Spine, Inc., Parsippany, NJ (US)

( * ) Notice: Subject to any disclaimer, the term of this patent is extended or adjusted under 35 U.S.C. 154(b) by 1750 days.

(21) Appl. No.: 11/947,987

(22) Filed: Nov. 30, 2007

(65) Prior Publication Data

US 2009/0143860 A1  Jun. 4, 2009

(51) Int. Cl.
*A61F 2/44* (2006.01)

(52) U.S. Cl.
USPC ..................... 623/17.16; 623/17.11

(58) Field of Classification Search
CPC ..... A61F 2/442; A61F 2/4455; A61F 2/4465; A61F 2/4611; A61F 2/4637; A61F 2002/30316; A61F 2002/2835; A61F 2002/30329; A61F 2002/30331; A61F 2002/30383; A61F 2002/30131; A61F 2002/30428; A61F 2002/4635; A61F 2002/30604; A61F 2002/448; A61F 2002/4475; A61F 2002/30975; A61F 2250/006
USPC ........................... 623/17.11–17.16
See application file for complete search history.

(56) References Cited

U.S. PATENT DOCUMENTS

| | | | |
|---|---|---|---|
| 6,395,031 B1 * | 5/2002 | Foley et al. | 623/17.11 |
| 6,554,863 B2 | 4/2003 | Paul et al. | |
| 6,648,916 B1 * | 11/2003 | McKay | 623/17.11 |
| 6,749,636 B2 * | 6/2004 | Michelson | 623/17.16 |
| 7,179,293 B2 * | 2/2007 | McKay | 623/17.11 |
| 7,300,465 B2 * | 11/2007 | Paul et al. | 623/17.11 |
| 2002/0091447 A1 * | 7/2002 | Shimp et al. | 623/17.16 |
| 2003/0120344 A1 * | 6/2003 | Michelson | 623/17.11 |
| 2004/0148029 A1 * | 7/2004 | Bianchi et al. | 623/17.11 |
| 2004/0186572 A1 * | 9/2004 | Lange et al. | 623/17.11 |
| 2005/0113918 A1 * | 5/2005 | Messerli et al. | 623/17.11 |
| 2005/0240267 A1 * | 10/2005 | Randall et al. | 623/17.11 |
| 2006/0241763 A1 * | 10/2006 | Paul et al. | 623/17.11 |

* cited by examiner

Primary Examiner — Pedro Philogene
Assistant Examiner — Lynnsy Schneider
(74) Attorney, Agent, or Firm — Rahman LLC

(57) ABSTRACT

A modular lateral expansion device to be inserted into an intervertebral space. The modular lateral expansion device includes a first member and a second member. The first end and the second end comprise a first extension and a second extension respectively. The first extension and second extension outwardly protrude from the first member in a same direction and are positioned at an axis transverse to a longitudinal axis of the first member. The second member comprises a first end and a second end. The first end comprises a plurality of outwardly extended arms and a first passage positioned between the plurality of outwardly extended arms. The first end of the second member is dimensioned and configured to couple to the first end of the first member. The second end comprises a second passage dimensioned and configured to accommodate the second extension of the first member.

5 Claims, 11 Drawing Sheets

MODULAR LATERAL EXPANSION DEVICE

BACKGROUND

1. Technical Field

The embodiments herein generally relate to medical devices, and, more particularly, to a modular lateral expansion device used during orthopedic surgeries.

2. Description of the Related Art

In lumbar interbody spinal fusion procedures, two adjacent vertebral bodies are fused together by entirely removing the degenerated intervertebral disc between two adjacent vertebrae and inserting an implant within the vertebral body. Lastly, fusion material (e.g., bone graft) may be placed within the vertebral body, which, along with the body's natural cells, promotes bone formation.

Generally, the greatest compressive strength in the spine lies within the outer 30% of the vertebral bodies. Due to variable soft tissue anatomy, it is often difficult, surgically, to sufficiently seat intervertebral body devices laterally to capture and utilize this portion of bone. Thus, poor placement and subsidence of implants can occur leading to implant failure and foraminal subsidence (e.g., narrowing of vertebral foramen). Implant failure can and does lead to catastrophic clinically failure and exceedingly difficult and potentially dangerous spinal revision strategies.

Conventional techniques use one-piece devices to fill the interbody space. The size of the space filled is dictated by multiple factors such as the surrounding soft tissues (e.g., great vessels, ureter, bowel, sympathetic nerves, etc.), aggressiveness of the surgeon during the surgery, and the type of implant chosen. These implants usually do not violate the vertebral endplate but typically do not reliably reach the outermost structurally significant area of bone. The devices are routinely placed centrally within the interbody space where they are commonly in contact only with the softest portion of bone, not the more structurally sound outer cortical apophyseal bone.

Various insertable implants are available in different shapes and configurations. Examples of such insertable implants are expandable cages which often have treads, teeth of spikes that engage the vertebral endplates. Generally, these cages can be screwed or inserted into the interbody via distraction tools only in the cephalocaudal direction (e.g., anteroposterior direction). Cages also typically require destruction of the vertebral endplate by tapping or cutting the structural bone, thus leading to a greater rate on implant subsidence and foraminal stenosis. Accordingly, there remains a need for a new modular lateral expansion device for placement between vertebral bodies within the vertebral body both in lateral and cephalocaudal directions for enhanced structural support of the spine.

SUMMARY

In view of the foregoing, an embodiment herein provides a modular lateral expansion device to be inserted into an intervertebral space. The modular lateral expansion device includes a first member and a second member. The first member includes a first end and a second end. The first end and the second end comprise a first extension and a second extension respectively. Both the first extension and the second extension are positioned at an axis transverse to a longitudinal axis of the first member. The first extension and the second extension outwardly protrude from the first member in the same direction.

The second member includes a first end and a second end. The first end comprises a plurality of outwardly extended arms positioned at an axis transverse to a longitudinal axis of the second member, and a first passage positioned between the plurality of outwardly extended arms. The first end of the second member is dimensioned and configured to couple to the first end of the first member, and the first passage is dimensioned and configured to accommodate the first extension of the first end of the first member. The second end of the second member comprises a second passage which is dimensioned and configured to accommodate the second extension of the second end of the first member. The second end of the second member is dimensioned and configured to couple to the second end of the first member.

The second end of the first member may further include an opening dimensioned and configured to receive an insertion tool. Each of the first member and the second member may include a plurality of channels dimensioned and configured to couple with a vertebral endplate. The first member and the second member may be dimensioned and configured in an E-shape and are adapted to couple with each other to form a central vacant core. The second member may further include a hollow section dimensioned and configured to receive and supply bone graft material into the central vacant core. The second member further includes an opening in the second end dimensioned and configured to receive an insertion tool and an inner hole dimensioned and configured to accommodate the insertion tool. The first member and the second member may include any of polyetheretherketone, titanium alloy, and carbon fiber materials.

In another aspect, an apparatus to structurally support a vertebral body having an outer portion comprises a first member and a second member. The first member comprises a first end having a first extension, and a second end. The second end includes an opening adapted to receive a first insertion tool, and a second extension positioned adjacent to the opening. The second member may be coupled to the first member. The second member includes a first end and a second end. The first end comprises two arms and a first passage disposed between the two arms. The first passage may be adapted to accommodate the first extension of the first member. The second end of the second member comprises a second passage and an opening. The second passage is adapted to accommodate the second extension of the first member and the opening is configured to receive a second insertion tool. The first member and the second member are adapted to be positioned in the outer portion of the vertebral body in a laterally expanded position.

The outer portion may include the outer 30% of cortical tissue of the vertebral body. Each of the first member and the second member may further include a plurality of channels configured along an outer surface of the first member and the second member. The plurality of channels may be adapted to couple with a vertebral endplate. The first member and the second member may include an E-shape and are adapted to couple with each other to form a central vacant core. The second member may further include a hollow section adjacent to the second passage, and an inner hole. The hollow section may be configured to receive and supply bone graft material into the central vacant core and the inner hole may be configured to accommodate the second insertion tool.

In yet another aspect, a method of performing a surgical procedure includes inserting an implant in an expanded position into an intervertebral body space, inserting bone graft material between a first member and a second member in the expanded position, distracting the implant in a lateral direction of the intervertebral body space to a non-expanded position to form a central vacant core, inserting bone graft material into the central vacant core formed in the non-expanded position, distracting the implant in a cephalocaudal direction of the intervertebral body space to the non-expanded position to form the central vacant core, inserting an insertion tool into the first member to facilitate insertion of the first member into the intervertebral body space, and inserting the insertion tool into the second member to facilitate insertion of the second member into the intervertebral body space.

The implant includes the first member and the second member. The first member is laterally displaced with respect to the second member. Both the first member and the second member may be positioned in an outer portion of the intervertebral body space in the expanded position. The first member includes a first end and a second end. Both the first end and the second end comprise a first extension and a second extension respectively. The first extension is positioned at an axis transverse to a longitudinal axis of the first member and the second extension is positioned parallel to the first extension. The second member includes a first end and a second end. The first end further comprises a plurality of arms and a first passage between the plurality of arms and the second end includes a second passage. The first end of the first member is adapted to couple to the first end of the second member. The second end of the first member is adapted to couple to the second end of the second member. The first passage of the second member is configured to accommodate the first extension of the first member.

The second end of the second member may further comprise a hollow section adjacent to the second passage. The hollow section may be configured to receive and supply bone graft material into the central vacant core and the second passage may be adapted to accommodate the second extension of the first member. The outer portion may comprise the outer 30% of cortical tissue of the intervertebral body space. The first member and the second member may comprise any of polyetheretherketone, titanium alloy, and carbon fiber materials.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which.

DETAILED DESCRIPTION OF PREFERRED EMBODIMENTS

Figure 1A:
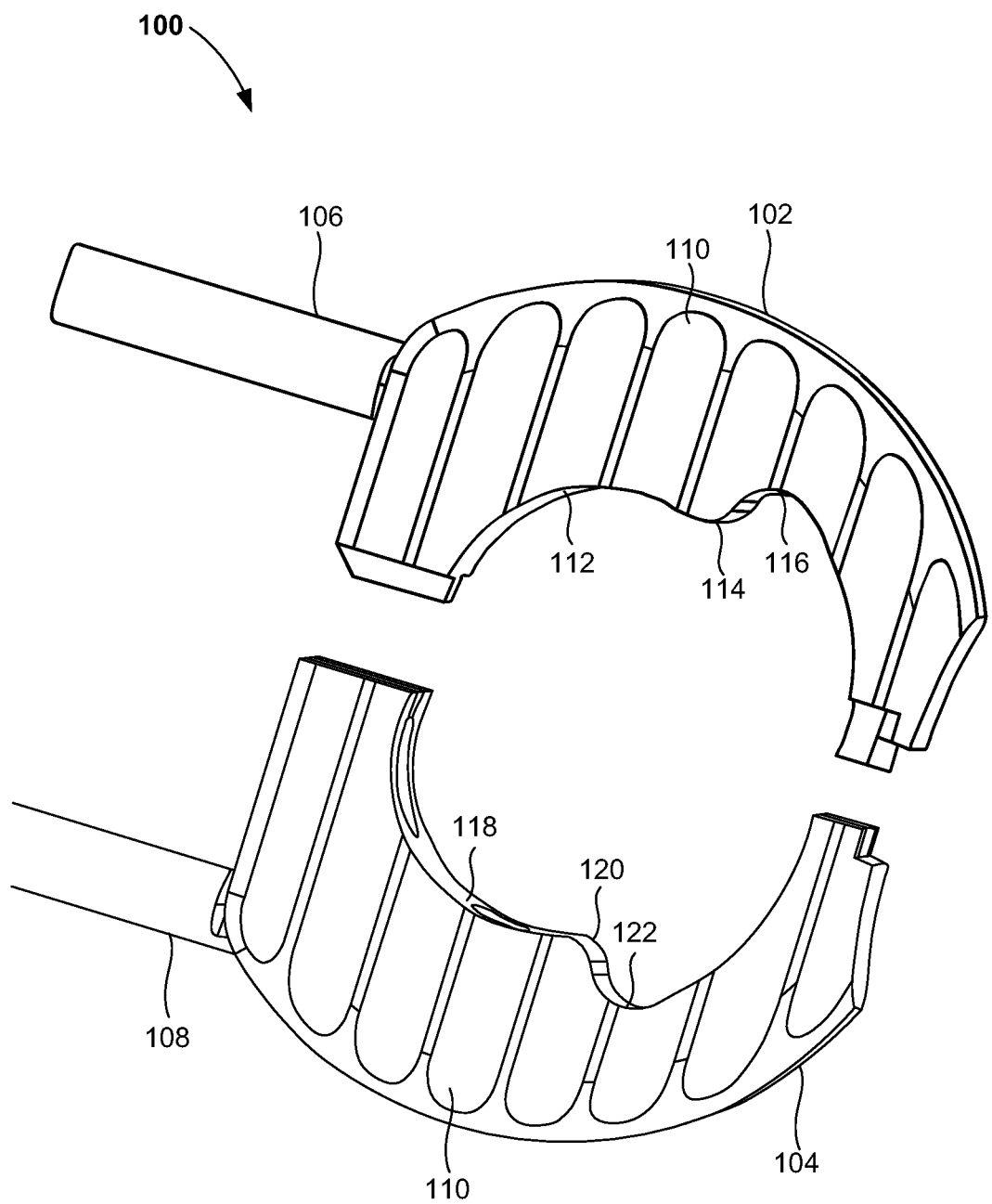
FIGS. 1A through 1C illustrate a top view, a sectional view, and a side view, respectively, of a modular lateral expansion device in an expanded position having a first member, a second member, a first rod, a second rod, and a plurality of channels according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for a new implant for increasing the enhanced structural support of the spine. The embodiments herein achieve this by providing a modular expandable intervertebral device that can be inserted into the spine and expanded in situ in both lateral and cephalocaudal directions. The modular lateral expansion device includes a first member and a second member. The first member includes a first end and a second end. The first end and the second end comprise a first extension and a second extension respectively. Both the first extension and the second extension are positioned at an axis transverse to a longitudinal axis of the first member. The first extension and the second extension outwardly protrude from the first member in the same direction. The second member includes a first end and a second end. The first end comprises a plurality of outwardly extended arms positioned at an axis transverse to a longitudinal axis of the second member, and a first passage positioned between the plurality of outwardly extended arms. The first end of the second member is dimensioned and configured to couple to the first end of the first member, and the first passage is dimensioned and configured to accommodate the first extension of the first end of the first member. The second end of the second member comprises a second passage which is dimensioned and configured to accommodate the second extension of the second end of the first member. The second end of the second member is dimensioned and configured to couple to the second end of the first member. Referring now to the drawings, and more particularly to FIG. 1A through FIG. 9, where similar reference characters denote corresponding features consistently throughout the figures, there are shown preferred embodiments.

Figure 1B:
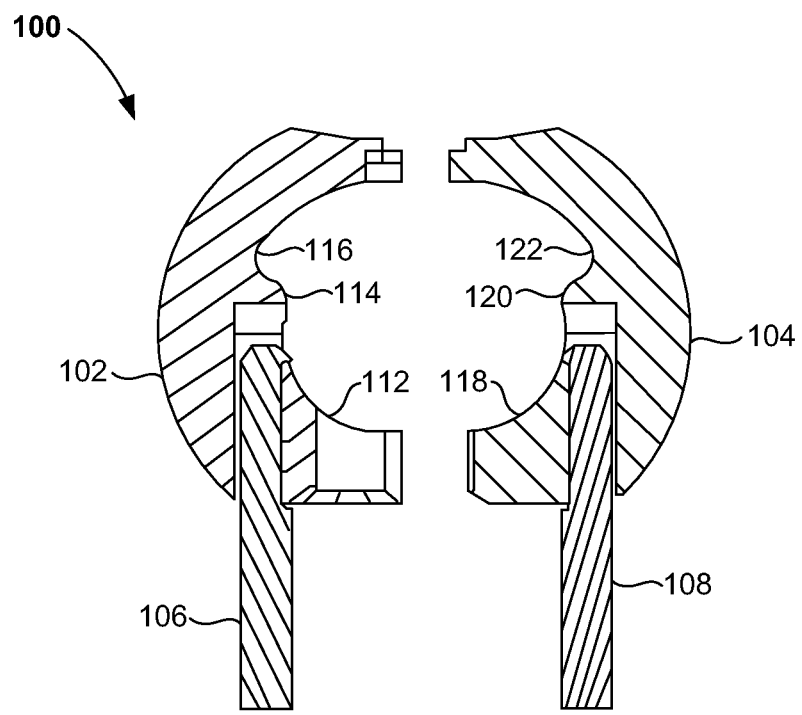
Figure 1C:
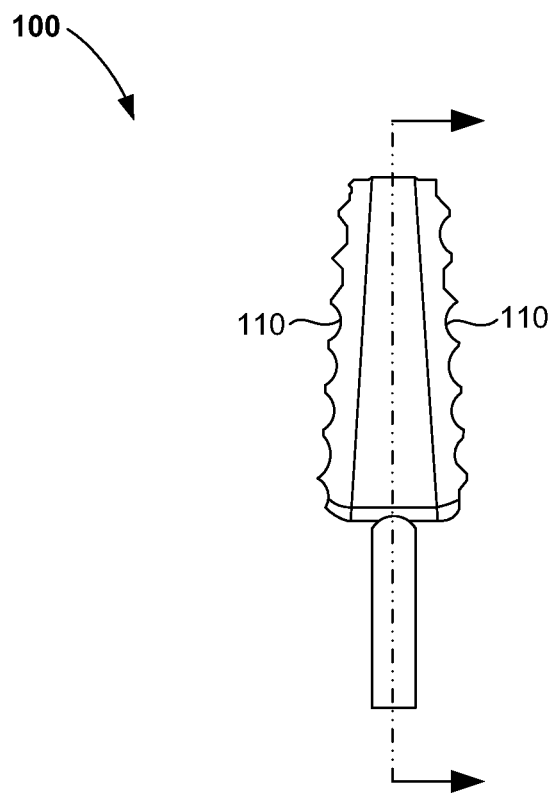
Figure 2:
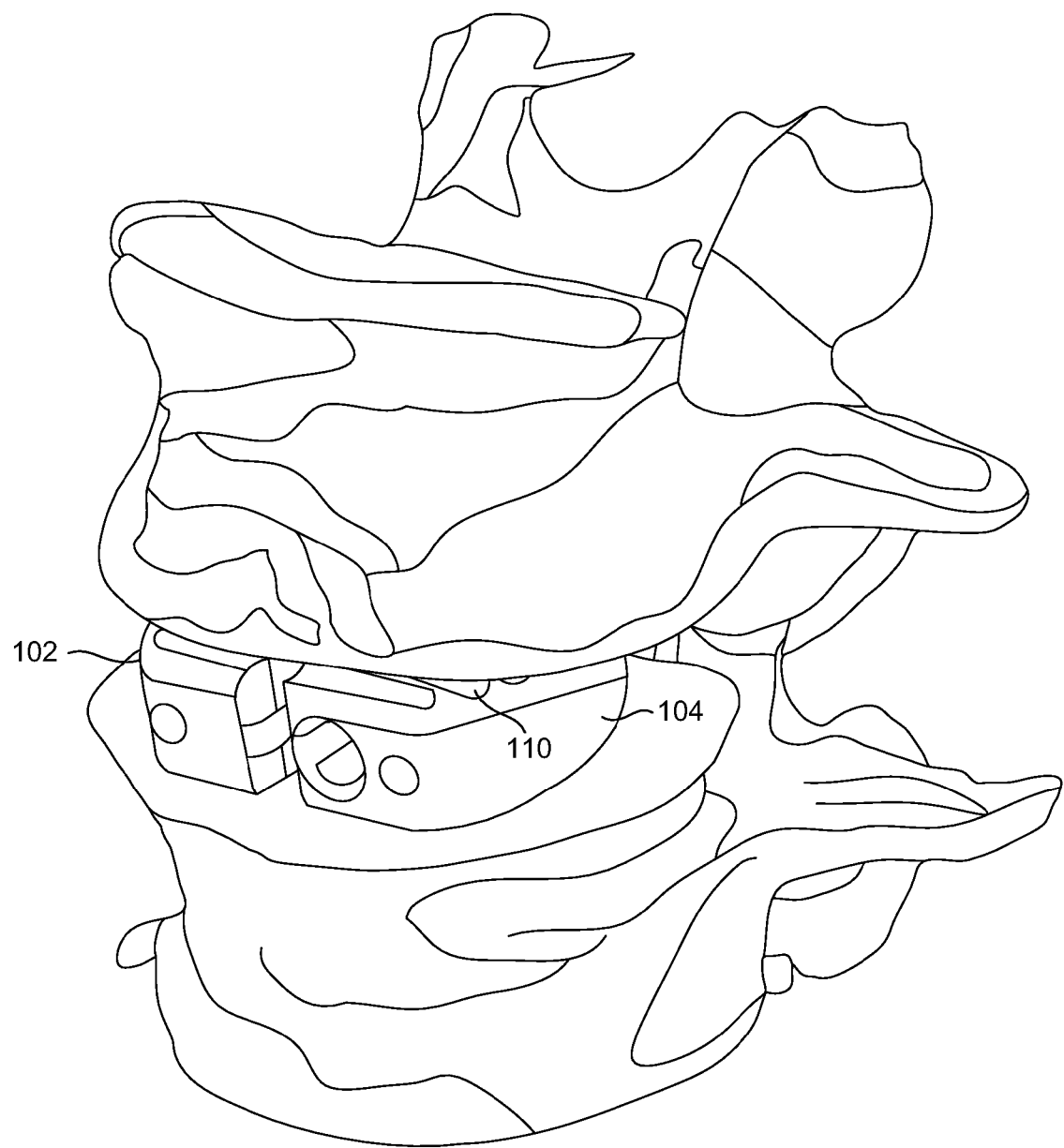
FIG. 2 illustrates a schematic diagram of the modular lateral expansion device of FIGS. 1A through 1C inserted into an intervertebral space according to an embodiment herein.

FIGS. 1A through 1C illustrate a top view, a sectional view, and a side view respectively of a modular lateral expansion device in an expanded position having a first member 102, a second member 104, a first rod 106, a second rod 108, and a plurality of channels 110 according to an embodiment herein. FIG. 2 illustrates a general view of the modular lateral expansion device of FIGS. 1A through 1C inserted into an intervertebral space according to an embodiment herein.

With reference to FIGS. 1A through 2, the first member 102 and the second member 104 may be generally curved and have an "E-shape". Both the first member 102 and the second member 104 include a plurality of channels 110 configured along an outer surface of the first member 102 and the second member 104. The channels 110 may be arranged in a direction transverse to the longitudinal axis of each member 102, 104.

The first member 102 further includes an inner wall 112, a bump 114, and a corresponding notch 116. Similarly the second member further includes an inner wall 118, a bump 120, and a corresponding notch 122. The "E-shape" of the members 102, 104 occurs due to the bump 114, 120 and corresponding notch 116, 122 formed along the inner walls 112, 118 of each member 102, 104, respectively. Moreover, the "E-shape" of the members 102, 104 allows the device 100 to better articulate with anatomy in the coronal and sagittal planes.

The first member 102 may connect with the first rod 106, and the second member 104 may connect with the second rod 108, wherein the rods 106, 108 are inserted into each respective member 102, 104. Preferably, the first rod 106 and the second rod 108 are positioned parallel to each other. Moreover, the first member 102 and the second member 104 are configured to connect to each other via lateral connection (i.e., connecting along an axis transverse to the longitudinal axis of each member 102, 104 and each rod 106, 108).

The modular lateral expansion device 100 is placed in a vertebral body (shown in FIG. 2) having an outer portion (e.g., the outer 30% of a cortical tissue of the vertebral body). The first member 102 along with the first rod 106 is laterally displaced with respect to the second member 104 with the second rod 108. The first and second rods 106 and 108, respectively, may act as insertion tools (e.g., devices used for inserting an implant into a vertebral body). In addition, the first rod 106 and the second rod 108 enable the modular lateral expansion device 100 to be placed and expanded in the vertebral body. The channels 110 may be dimensioned and configured to couple with a vertebral endplate. Additionally, the channels 110 are of non-uniform length.

In one embodiment, the modular lateral expansion device 100 is constructed using materials such as PEEK™ (Polyetheretherketon) plastic available from Whitford Worldwide Company, Delaware, USA, titanium alloy, or carbon fiber, etc. The modular lateral expansion device 100 has the capacity to separate in a controlled manner in situ (e.g., in the original position) in the sagittal plane (e.g., a plane that divides the body of a bilaterally symmetrical animal into right and left portions). This is accomplished due to the alignment of the first and second members 102, 104.

Figure 3A:
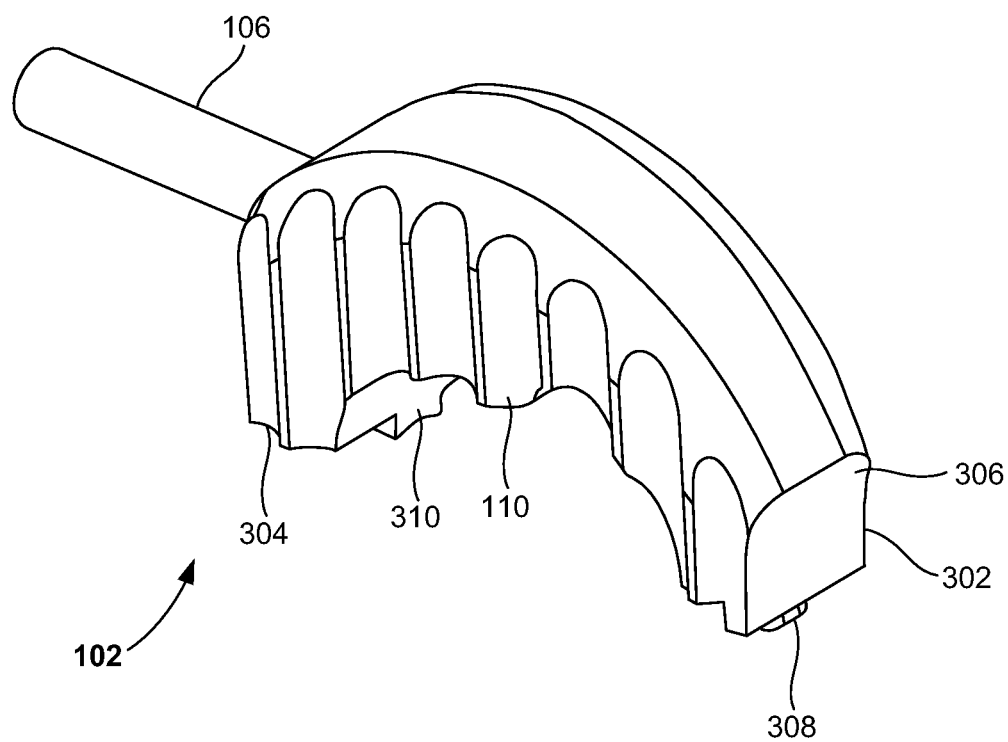
FIGS. 3A through 3B illustrate perspective views of the first member of FIGS. 1A through 2 according to an embodiment herein.
Figure 3B:
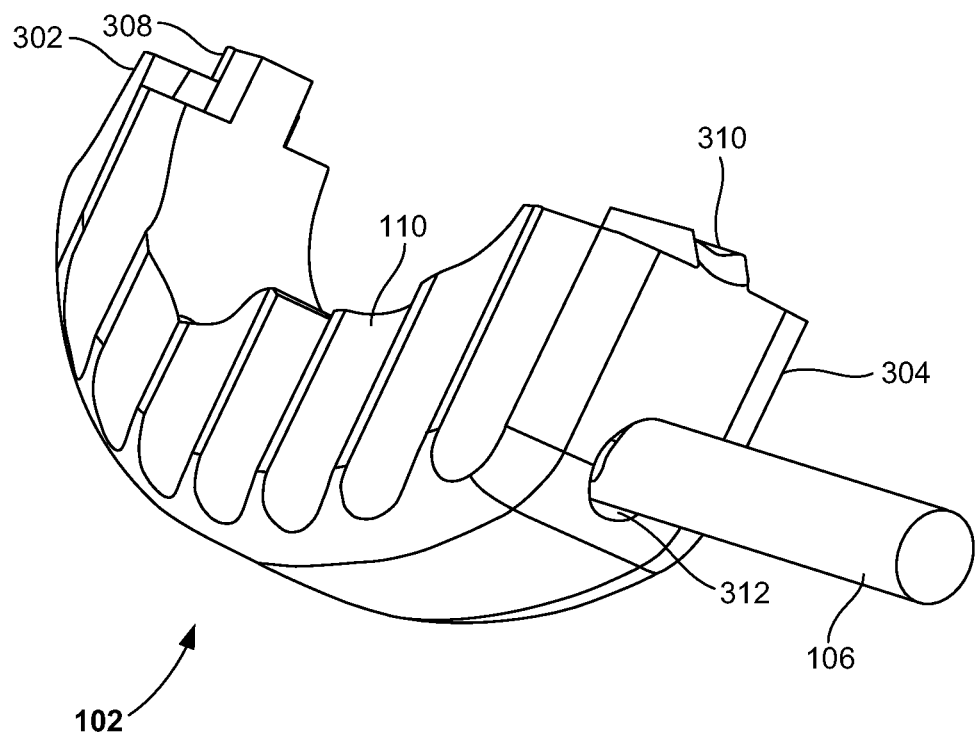

FIGS. 3A through 3B illustrate perspective views of the first member 102 of FIGS. 1A through 2 according to an embodiment herein. The first member 102 includes a first end 302 having a curved plane 306, a first extension 308, and a second end 304 having a second extension 310 and an opening 312, and the channels 110. The channels 110 are positioned between the first end 302 and the second end 304. The second end 304 is wider than the first end 302. At one side of the second end 304 the second extension 310 is present while at the other side the opening 312 is present. The first extension 308 and the second extension 310 outwardly protrude from the first member 102 in the same direction and are positioned at an axis transverse to a longitudinal axis of the first member 102. The second extension 310 and opening 312 are in transverse planes with respect to one another. The opening 312 is dimensioned and configured to receive the first rod 106.

Figure 4A:
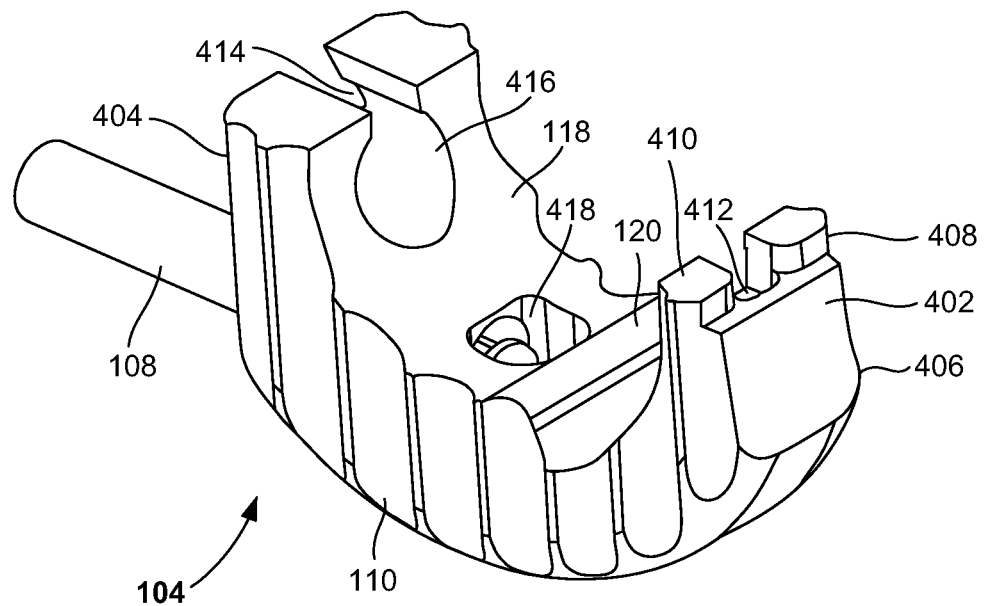
FIGS. 4A through 4B illustrate perspective views of the second member of FIGS. 1A through 2 according to an embodiment herein.
Figure 4B:
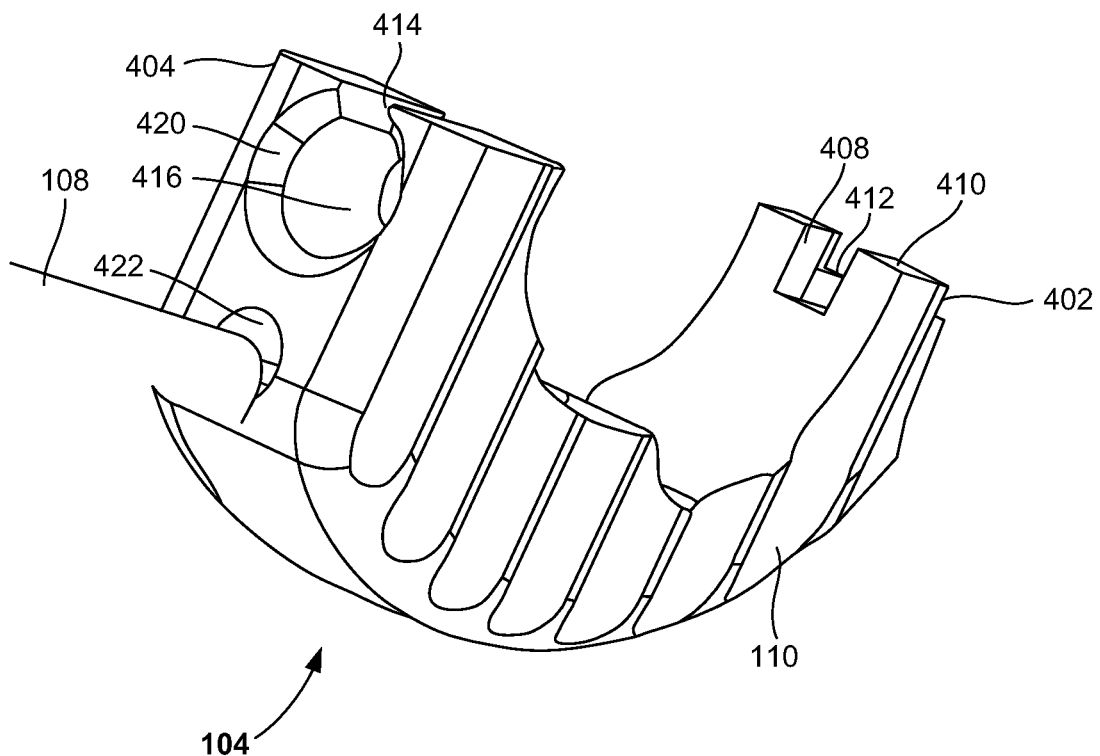

FIGS. 4A through 4B illustrate perspective views of the second member 104 of FIGS. 1A through 2 according to an embodiment herein. The second member 104 includes a first end 402 having a curved plane 406, and a second end 404. The second end 404 is wider than the first end 402. The channels 110 are positioned between the first end 402 and the second end 404. The first end 402 includes two outwardly extended arms 408, 410 positioned at an axis transverse to a longitudinal axis of the second member 104. The first member 102 includes a first passage 412 positioned between the two outwardly extended arms 408, 410. The two arms 408, 410 are present just below the curved plane 406 and extend beyond the curved plane 406.

The second end 404 includes a second passage 414, a hollow section 416, an inner hole 418, a cavity 420 surrounding the hollow section 416, and an opening 422. The inner hole 418 is present at the inner wall 118 of the second member 104. The cavity 420 surrounds the hollow section 416. The second passage 414 cuts the hollow section 416 and the cavity 420. The opening 422 receives the second rod 108. The second rod 108 passing through the opening 422 becomes fixed (via press fitting) into the inner hole 418.

The first end 402 of the second member 104 is dimensioned and configured to couple to the first end 302 of the first member 102, and similarly the second end 404 of the second member 104 is dimensioned and configured to couple to the second end 304 of the first member 102. The first passage 412 is dimensioned and configured to accommodate the first extension 308 of the first member 102 and the second passage 414 is dimensioned and configured to accommodate the second extension 310 of the first member 102. The hollow section 416 may be dimensioned and configured to receive bone graft material. The opening 422 is dimensioned and configured to receive the second rod 108 and the inner hole 418 is dimensioned and configured to accommodate the second rod 108.

Figure 5A:
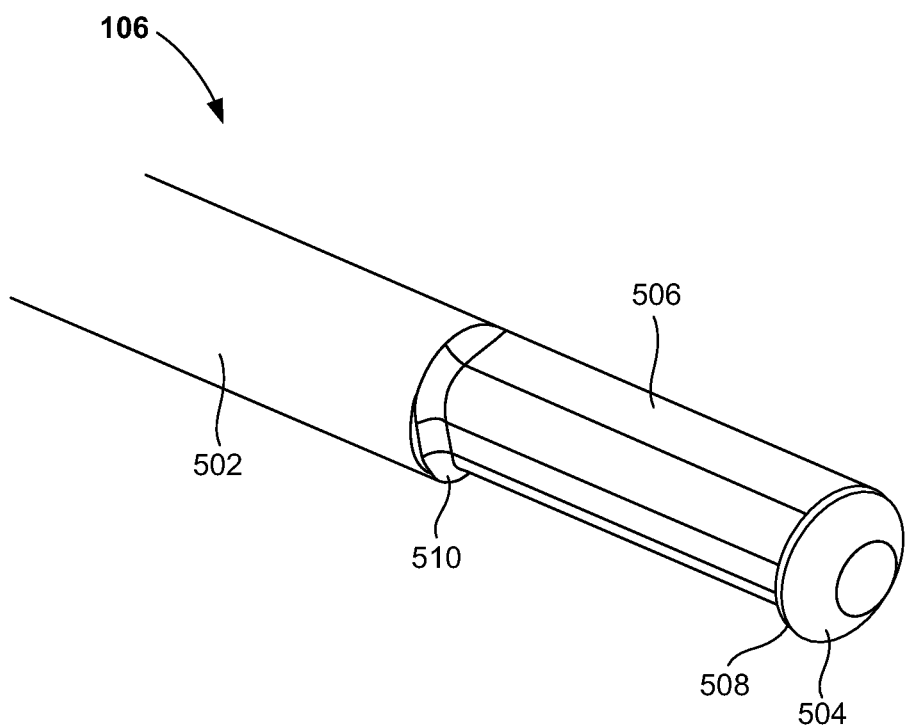
FIGS. 5A through 5B illustrate perspective views of the first rod and the second rod respectively of FIGS. 1A through 1C according to an embodiment herein.
Figure 5B:
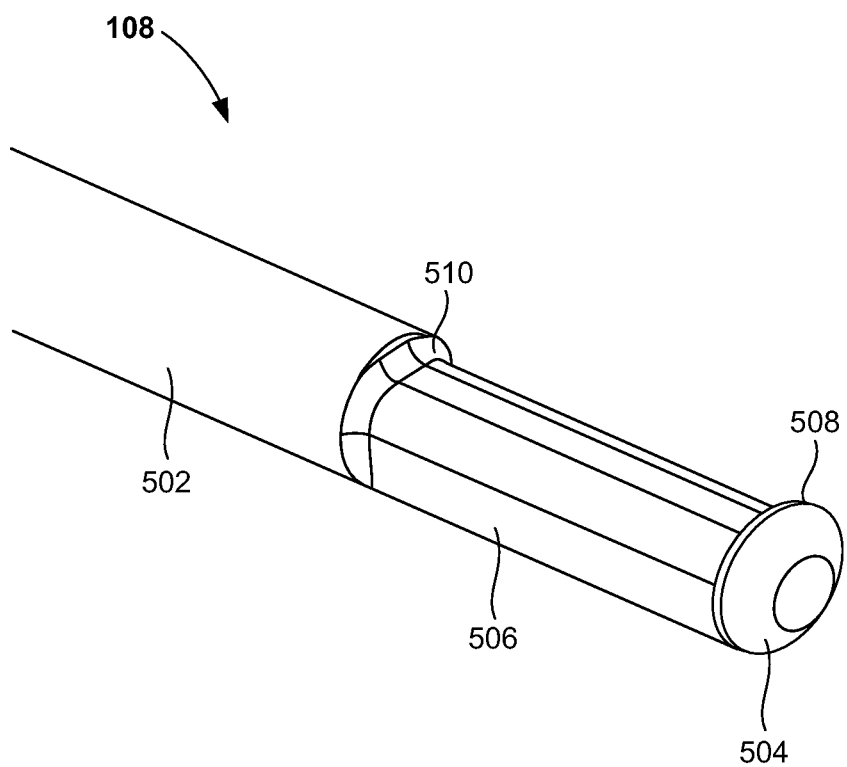
Figure 6A:
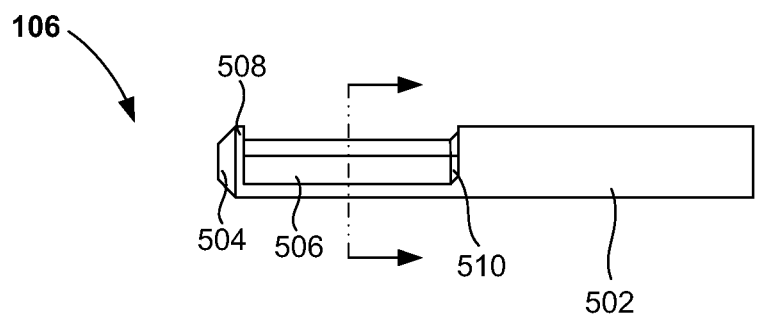
FIGS. 6A through 6C illustrate a side view, a back view, and a sectional view, respectively, of any one of the first rod and the second rod of FIGS. 1A through 1C according to an embodiment herein.
Figure 6C:
Figure 6B:
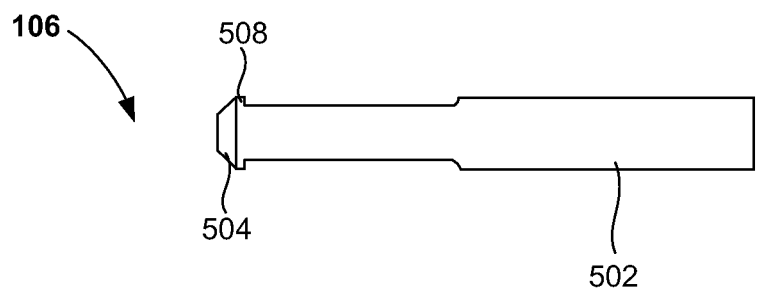

FIGS. 5A through 5B illustrate front views of the first rod 106 and the second rod 108, respectively, of FIGS. 1A through 1C according to an embodiment herein. FIGS. 6A through 6C illustrate a side view, a back view, and a sectional view, respectively, of any one of the first rod 106 and the second rod 108 of FIGS. 1A through 1C according to an embodiment herein.

With reference to FIGS. 5A through 6C, the first rod 106 and the second rod 108 are identical and parallel to each other. The first rod 106 and the second rod 108 each include a cylindrical structure 502 with a head 504. A segment 506 is present below the head 504. The head 504 includes a catch 508 at the top. The segment 506 is attached to the cylinder 502 at a base 510. The segment 506 at one side has a width less than the head 504 and the cylinder 502. The head 504 of the second rod 108 is set into the inner hole 418 of the second member 104 (e.g., as shown in FIG. 4A) which may prevent the premature decoupling of the second rod 108 from the second member 104. Preferably, the first member 102 has a similar hole (not shown but similar to the inner hole 418 of the second member 104). Premature decoupling of the rods 106, 108 can be prevented by proper angled rotation of the rods 106, 108 to ensure that the catch 508 (shown in FIGS. 5A and 5B) remain hooked in the inner hole 418 of the second member 104 (and corresponding inner hole 418 (not shown) in the first member 102).

Figure 7A:
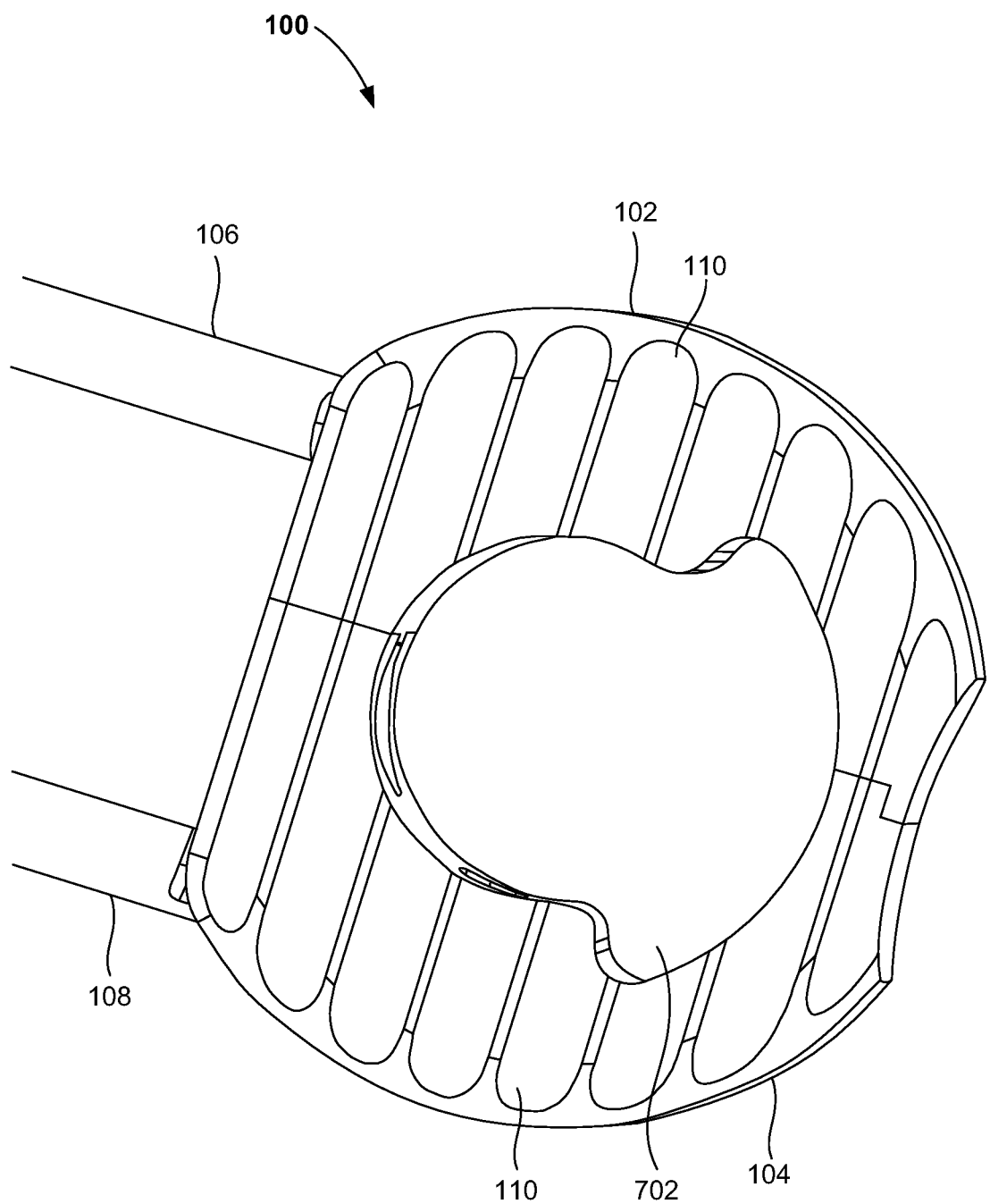
FIG. 7A through 7C illustrate a top view, a sectional view, and a side view, respectively, of the modular lateral expansion device of FIGS. 1A through 1C in an assembled (i.e., non-expanded) position according to an embodiment herein.
Figure 7B:
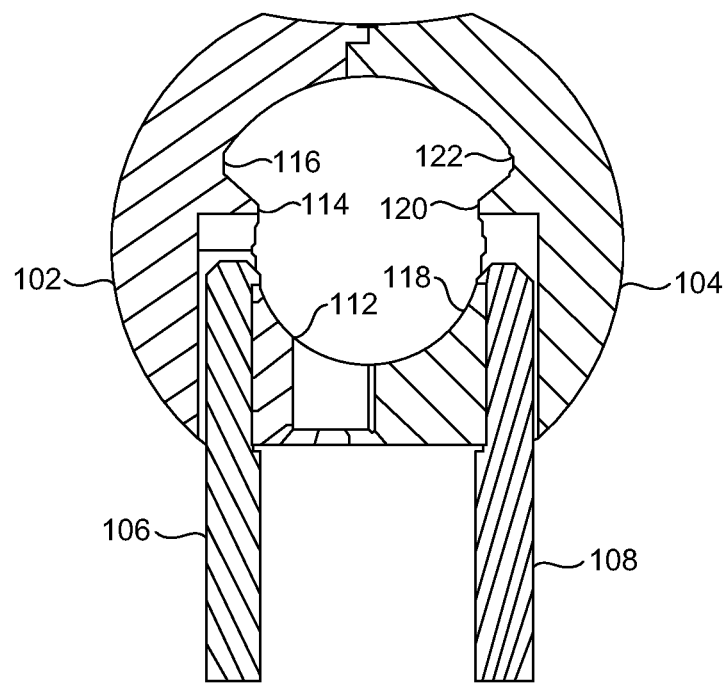
Figure 7C:
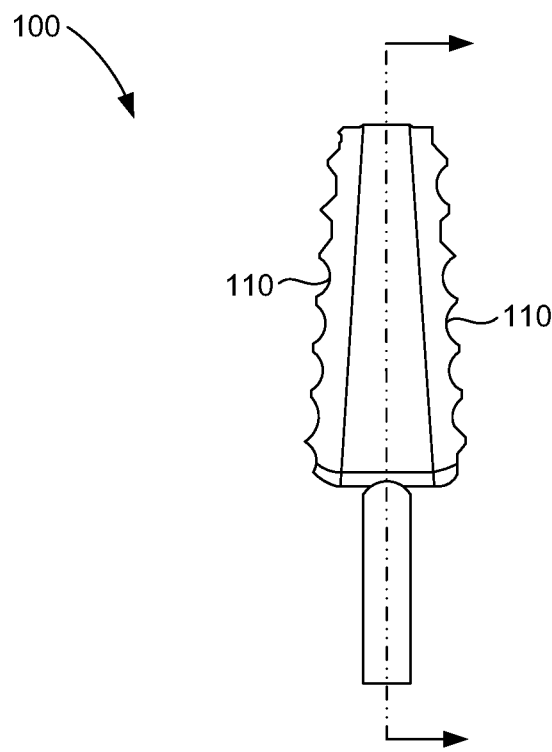
Figure 8:
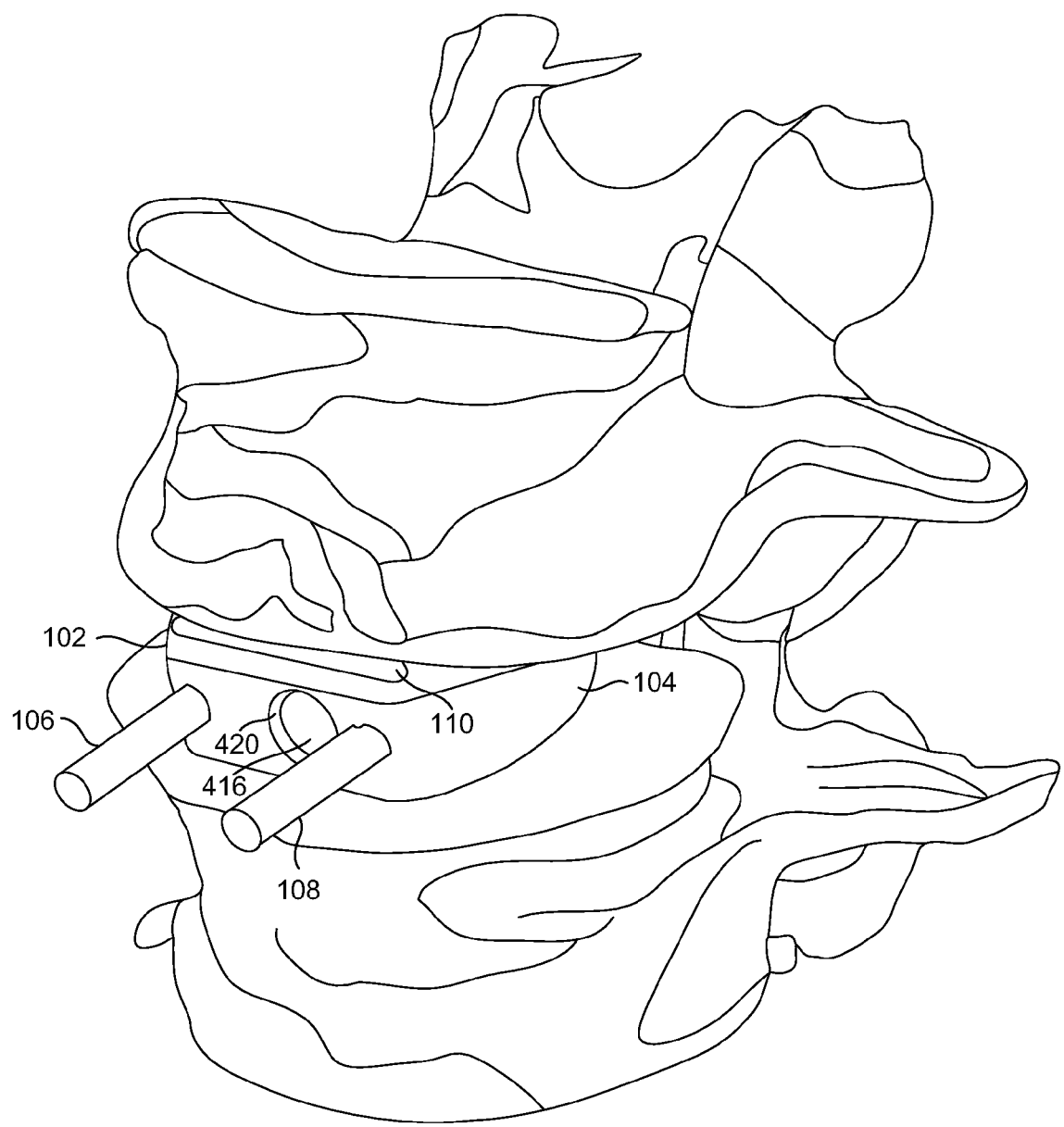
FIG. 8 illustrates a schematic diagram of the modular lateral expansion device of FIGS. 7A through 7C inserted into an intervertebral space according to an embodiment herein.

FIGS. 7A through 7C, with reference to FIGS. 1A through 6C, illustrate a top view, a sectional view, and a side view, respectively, of the modular lateral expansion device 100 of FIGS. 1A through 1C in an assembled (i.e., non-expanded) position according to an embodiment herein. FIG. 8 illustrates a general view of the modular lateral expansion device 100 of FIGS. 7A through 7C inserted into an intervertebral space according to an embodiment herein. With reference to FIGS. 7A through 8, the first end 302 of the first member 102 is fixed with the first end 402 of the second member 104. Similarly, the second end 304 of the first member 102 and the second end 404 of the second member 104 are fixed with each other. The curved plane 306 and the curved plane 406 are in same level thereby creating a contoured surface. The first passage 412 between the two arms 408, 410 of the second member 104 accommodates the first extension 308 of the first member 102. Similarly, the second extension 310 fits into the second passage 414.

The curved plane 306 of the first member 102 is fixed over the two arms 408, 410 of the second member 104. The shape of the second extension 310 exactly matches with the second passage 414 to complete the cavity 418 with the hollow section 416. The first member 102 and the second member 104 are locked with each other for maintaining the spatial relationship. Additionally, the first member 102 and the second member 104 are coupled with each other to form a central vacant core 702. The modular lateral expansion device 100 can be placed both in lateral and cephalocaudal directions within the vertebral body and the position of the modular lateral expansion device 100 can be maintained with the help of the first rod 106 and the second rod 108.

Once the modular lateral expansion device 100 is placed within the outer portion of the vertebral body, it can distract and the first member 102 can be separated and laterally displaced with respect to the second member 104 (e.g., as shown in FIG. 1) via maneuvering of the rods 106, 108. Further bone grafting may be allowed by filling the central vacant core 702 with bone grafting material (not shown) which allows for greater fusion surface area compared with conventional devices that are merely semi-circular (or C-shaped). The bone grafting material may be received through the hollow section 416 and supplied into the central vacant core 702.

The device 100 is smaller than other comparable conventional devices. As an example, in the open configuration of FIGS. 1A through 2, the device 100 may be dimensioned and configured to have an overall length in the range of approximately 30.70 mm to 31.05 mm and an overall width of approximately 47.00 mm. In the closed configuration of FIGS. 7A through 8, the device 100 may be dimensioned and configured to have an overall length in the range of approximately 30.70 mm to 31.05 mm and an overall width of approximately 37.00 mm.

Figure 9:
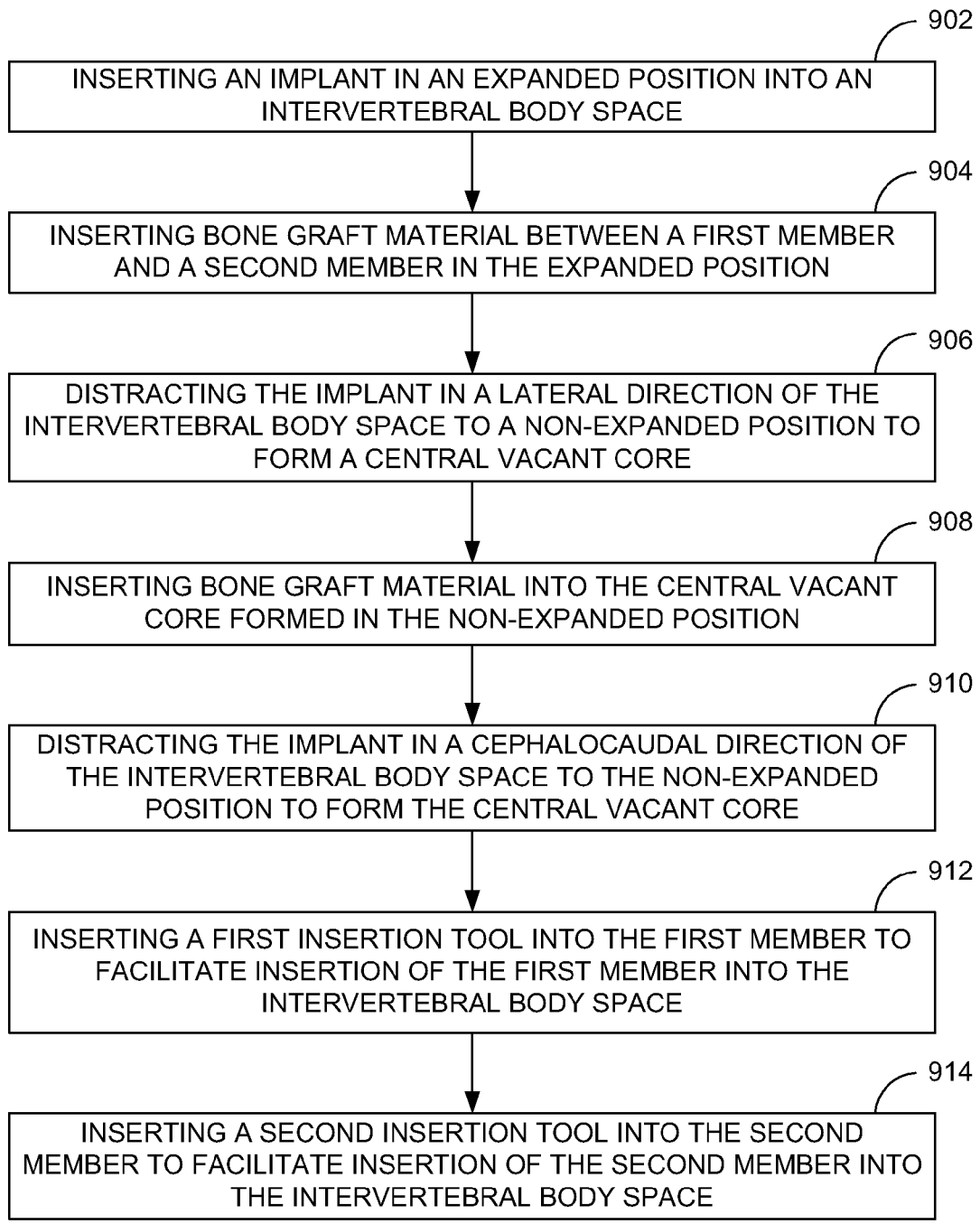
FIG. 9 is a process flow diagram that illustrates a method of performing a surgical procedure according to an embodiment herein.

FIG. 9, with reference to FIGS. 1A through 8, is a process flow diagram that illustrates a method of performing a surgical procedure according to an embodiment herein, wherein the method comprises inserting (902) an implant 100 in an expanded position into an intervertebral body space, inserting (904) bone graft material between a first member 102 and a second member 104 in the expanded position, distracting (906) the implant 100 in a lateral direction of the intervertebral body space to a non-expanded position to form a central vacant core 702, inserting (908) bone graft material into the central vacant core 702 formed in the non-expanded position, distracting (910) the implant 100 in a cephalocaudal direction of the intervertebral body space to the non-expanded position to form the central vacant core 702, inserting (912) a first insertion tool (e.g., the first rod 106) into the first member 102 to facilitate insertion of the first member 102 into the intervertebral body space, and inserting (914) a second insertion tool (e.g., the second rod 108) into the second member 104 to facilitate insertion of the second member 104 into the intervertebral body space.

In step 902, the implant 100 having the first member 102 and the second member 104 is inserted into an intervertebral body space in the expanded position. In step 904, bone graft material is inserted between the first member 102 and the second member 104 in the expanded position. In step 906, the implant 100 is distracted in a lateral direction of the intervertebral body space to the non-expanded position to form the central vacant core 702 (between the first member 102 and the second member 104). In step 908, the bone graft material is inserted into the central vacant core 702 formed in the non-expanded position (e.g., through the hollow section 416 of the second member 104). In step 910, the implant 100 may be distracted in a cephalocaudal direction of the intervertebral body space to the non-expanded position to form the central vacant core 702. In step 912, the first rod 106 may be inserted into the first member 102 (e.g., through the opening 312 of the first member 102 as illustrated in FIG. 3B) to facilitate insertion of the first member 102 into the intervertebral body space. In step 914, the second rod 108 may be inserted into the second member 104 (e.g., through the opening 422 of the second member 104 as illustrated in FIG. 4B) to facilitate insertion of the second member 104 into the intervertebral body space.

The modular lateral expansion device 100 can be distracted bi-directionally both in lateral and cephalocaudal directions in situ. It also solves the problems of subsidence and poor placement by allowing for lateral reproducible placement of the first member 102 and the second member 104. During direct central placement with the vertebral endplate (not shown), the channels 110 of the modular lateral expansion device 100 accommodate the vertebral endplate, thereby not requiring a cutting device and decreasing risk of implant failure.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the amended claims.

What is claimed is:

1. A modular lateral expansion device adapted to be inserted into an intervertebral space, said modular lateral expansion device comprising:
   a first member comprising:
      a first end comprising a first extension positioned at an axis transverse to a longitudinal axis of said first member, wherein said first extension comprises a first concaved surface of a first radius on an inner surface of said first member; and
      a second end comprising a second extension positioned at an axis transverse to said longitudinal axis of said first member, wherein said second extension comprises a second concaved surface of a second radius on said inner surface of said first member, wherein said first extension and said second extension outwardly protrude from said first member in a same direction, wherein said first radius is larger than said second radius, and wherein said second end of said first member is wider than said first end of said first member; and a second member comprising:

a first end comprising a plurality of outwardly extended arms positioned at an axis transverse to a longitudinal axis of said second member, and a first passage positioned between said plurality of outwardly extended arms, wherein said first end of said second member is dimensioned and configured to couple to said first end of said first member, and wherein said first passage is dimensioned and configured to accommodate said first extension of said first end of said first member; and a second end comprising a second passage, wherein said second end of said second member is dimensioned and configured to couple to said second end of said first member, and wherein said second passage is dimensioned and configured to accommodate said second extension of said second end of said first member, and wherein the second end of said second member is wider than the first end of said second member, wherein said first member and said second member are dimensioned and configured in an E-shape and are adapted to couple with each other to form a central vacant core, wherein said second member comprises a hollow section, wherein said hollow section is dimensioned and configured to receive and supply bone graft material into said central vacant core, and wherein said hollow section is cut by said second passage.

2. The modular lateral expansion device of claim 1, wherein said second end of said first member further comprises an opening dimensioned and configured to receive an insertion tool.

3. The modular lateral expansion device of claim 1, wherein each of said first member and said second member comprise a plurality of channels dimensioned and configured to couple with a vertebral endplate, and wherein said plurality of channels are configured along an outer surface of said first member and said second member.

4. The modular lateral expansion device of claim 1, wherein said second member further comprises:

an opening in said second end dimensioned and configured to receive an insertion tool; and an inner hole dimensioned and configured to accommodate said insertion tool.

5. The modular lateral expansion device of claim 1, wherein said first member and said second member comprise any of polyetheretherketone, titanium alloy, and carbon fiber materials.

\* \* \* \* \*